(12) United States Patent
Cauchard et al.

(10) Patent No.: US 7,887,858 B2
(45) Date of Patent: Feb. 15, 2011

(54) COSMETIC COMPOSITION CONTAINING AN AMBER EXTRACT

(75) Inventors: Jean-Hubert Cauchard, Orleans (FR); Frédéric Bonte, Orleans (FR); Jean-Christophe Archambault, Meung sur Loire (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 11/888,181

(22) Filed: Jul. 31, 2007

(65) Prior Publication Data

US 2008/0181974 A1    Jul. 31, 2008

(30) Foreign Application Priority Data

Jan. 30, 2007    (FR) .................................. 07 52973

(51) Int. Cl.
A61K 36/899 (2006.01)
A61K 36/484 (2006.01)
C09F 1/00 (2006.01)

(52) U.S. Cl. .................. 424/750; 424/757; 530/203

(58) Field of Classification Search .................. None
See application file for complete search history.

(56) References Cited

U.S. PATENT DOCUMENTS

| 6,004,568 | A | 12/1999 | Bonte et al. | |
|---|---|---|---|---|
| 6,193,975 | B1 | 2/2001 | Bonte et al. | |
| 6,630,163 | B1 * | 10/2003 | Murad | 424/464 |
| 2003/0004449 | A1 | 1/2003 | Lafratta et al. | |
| 2005/0266065 | A1 * | 12/2005 | Perrier et al. | 424/450 |

FOREIGN PATENT DOCUMENTS

| CN | 1245052 | | 2/2000 |
|---|---|---|---|
| CN | 1325678 | | 12/2001 |
| CN | 1325678 | A | 12/2001 |
| JP | 9-227334 | A | 9/1997 |
| JP | 9227334 | | 9/1997 |
| WO | WO 02/085314 | * | 10/2002 |
| WO | WO 02/085314 | A1 | 10/2002 |

OTHER PUBLICATIONS

Vesper et al. Sphingolipids in Food and the Emerging Importance of Sphingolipids to Nutrition. The Journal of Nutrition. Jul. 1999; 129,7 pp. 1239-1250.*

Beck., "The Chemistry of Amber" Est.Mus.Cienc. Nat. de Alava (1999), 14 (Num Espec. 2): 33-48.

Mills et al., "The Chemical Composition of Baltic Amber" Chemical Geology 47 (1984/85) 15-39.

* cited by examiner

*Primary Examiner*—Christopher R Tate
*Assistant Examiner*—Melenie McCormick
(74) *Attorney, Agent, or Firm*—Hamre, Schumann, Mueller & Larson, P.C.

(57) ABSTRACT

A cosmetic composition includes as active agents, a first active agent consisting of an amber extract, and at least one other cosmetically active agent selected from the group consisting of extracts of *Bertholletia excelsa*, extracts of *Potentilla erecta*, magnesium aspartate, peptides acting on muscle contraction, particularly acetyl hexapeptide 3, peptides and their derivatives grafted with a fatty acid, particularly a $C_{16}$ fatty acid, promoting collagen synthesis, particularly palmitoyl oligopeptide pentapeptide 3 or palmitoyl tetrapeptide 7, soy flour hydrolyzates and plant glycolipids, particularly cereal glycosphingolipids and more particularly wheat glycosphingolipids. An amber extract also may be used as a cosmetic agent acting on the dermal supporting proteins and/or the enzymatic systems that degrade the dermal proteins and/or the glycan-type essential components of the extracellular matrix, particularly proteoglycans, for improving the essential biomechanical properties of the skin, namely firmness and elasticity, in the preparation of a cosmetic composition.

9 Claims, No Drawings

COSMETIC COMPOSITION CONTAINING AN AMBER EXTRACT

The present invention relates to a cosmetic composition comprising an amber extract. It further relates to the use of such an extract as a cosmetic agent, especially for improving skin firmness.

Cosmetic composition formulators generally seek to associate active agents having complementary properties within one and the same cosmetic composition so as to optimize the efficacy of this composition.

Thus it is common to find, in one and the same cosmetic composition, active agents that give this composition complementary effects, e.g. skin moisturizing properties and anti-wrinkle properties.

It is also common to seek to associate, for a specific purpose, e.g. firming the skin, different active agents which already have this activity, or a similar activity, but which are known to act by different mechanisms, so as to achieve an optimum result.

It is known that the appearance of wrinkles and loss of skin firmness is generally recognized as a problem originating in the dermis, which essentially consists of collagen proteins synthesized by the fibroblasts, immersed in a hydrated extracellular matrix and kept under tension by the fibroblasts. During the ageing process, there are fewer supporting proteins, the enzymatic degrading systems are hyperactivated and the skin loses density, which is why it is necessary to find novel active agents that are capable of acting on these principal parameters.

The invention results from systematic experiments performed by the inventors of the present invention in order to find the most effective active ingredient possible for acting on the different parameters mentioned above, in a cosmetic composition already containing at least one active agent for improving skin condition, and more particularly at least one active agent selected from the group consisting of:

- an extract of *Bertholletia excelsa*, particularly an extract of the pericarp of the fruit, known to promote collagen synthesis,
- an extract of *Potentilla erecta* (tormentille), known for its action on collagen synthesis,
- magnesium aspartate, known for its action on the cohesion between the dermis and the epidermis,
- a peptide known to slow down the release of neuromediators and promoting muscle contraction, particularly acetyl hexapeptide 3, better known under the tradename ARGIRELINE®,
- a peptide or one of its derivatives grafted with a fatty acid, particularly a $C_{16}$ fatty acid, or a combination of such peptides, for promoting collagen synthesis, particularly palmitoyl oligopeptide pentapeptide 3 or palmitoyl tetrapeptide 7,
- a soy flour hydrolyzate rich in glycoproteins, known to act on collagen I synthesis, and
- plant glycopeptides, particularly wheat glycosphingolipids, known to strengthen the stratum corneum.

In their search to improve the efficacy of cosmetic compositions containing at least one of the active agents mentioned above, with a view to improving skin firmness, the inventors of the present invention noticed that amber extracts were particularly valuable candidates.

They were also able to correlate these particularly valuable properties of amber extracts with the result of tests which made it possible to show, totally unexpectedly, that an amber extract had a remarkable modulating activity on the gene expression profile of human dermal fibroblasts cultivated in a monolayer, acting simultaneously at several levels.

Amber derives its name from the Arabic aribar. It is a fossilized resin originating from ancient trees with the collective name *Pinus succinifera*, which developed in what were known as "the amber forests". In fact, about 45 million years ago, the entire Central European region was covered with forests. It is not known exactly which tree or trees were responsible for the formation of this amber, but, contrary to popular opinion, amber probably originates not from the pine sap but from the vascular tissue of the trees, exuded particularly during radical climate changes. Generic descriptions of the composition of amber have been published (cf., in particular, C. W. Beck, The chemistry of amber, Est. Mus. Cienc. nat. de Alava, 1999, num. espec. 2, 33-48, and J. S. Mills, The chemical composition of Baltic amber, Chemical geology, 1984, 47, 15-39).

90% of the world's amber resources are concentrated in a Russian territorial enclave located to the north of the Baltic Sea and surrounded by Poland and Lithuania. It is extracts of amber from this region which were used within the framework of the present invention and are hereafter referred to as extracts of Baltic amber.

The use of amber or amber extracts in cosmetic compositions had already been described prior to the present patent application.

Thus Japanese patent application JP 09-227334 described the use of amber extracts, obtained with organic solvents, for its antibacterial, antioxidant and deodorant effects.

Chinese patent application CN 1245052 described the use of an amber powder for its antiwrinkle action.

Chinese patent application CN 1325678 described the use of an alcoholic amber extract for strengthening the protective shield formed by the skin, and improving the microcirculation in the skin.

Thus, even though these various documents teach that it was known, prior to the present invention, to use amber powder or an amber extract in cosmetic compositions, none of these documents suggests the particular activities on the constituents of the dermis which have been demonstrated by the inventors of the present invention, or their consequences on the efficacy of certain associations that form the subject of the present patent application, said efficacy resulting from the non-obvious simultaneous properties demonstrated by the inventors of the present patent application.

Thus, according to one of its essential characteristics, the invention relates to a cosmetic composition comprising the following as active agents:

- a first active agent consisting of an amber extract, and
- at least one other active agent selected from the group consisting of extracts of *Bertholletia excelsa*, extracts of *Potentilla erecta*, magnesium aspartate, peptides acting on muscle contraction, particularly acetyl hexapeptide 3, peptides and their derivatives grafted with a fatty acid, particularly a $C_{16}$ fatty acid, promoting collagen synthesis, particularly palmitoyl oligopeptide pentapeptide 3 or palmitoyl tetrapeptide 7, soy flour hydrolyzates and plant glycolipids, particularly cereal glycosphingolipids and more particularly wheat glycosphingolipids.

According to another essential characteristic, the invention further relates to the use of an amber extract, especially an extract of Baltic amber, as a cosmetic agent acting on the dermal supporting proteins and/or the enzymatic systems that degrade the dermal proteins and/or the glycan-type essential components of the extracellular matrix, particularly proteoglycans, for improving the essential biomechanical properties of the skin, namely firmness and elasticity, in the preparation of a cosmetic composition, especially a cosmetic composition comprising at least one active agent selected from the group consisting of extracts of *Bertholletia excelsa*, extracts of *Potentilla erecta*, magnesium aspartate, peptides acting on muscle contraction, particularly acetyl hexapeptide 3, peptides and their derivatives grafted with a fatty acid, particularly a $C_{16}$ fatty acid, promoting collagen synthesis, particularly palmitoyl oligopeptide pentapeptide 3 or palmitoyl tetrapeptide 7, soy flour hydrolyzates and plant glycolipids, particularly cereal glycosphingolipids and more particularly wheat glycosphingolipids.

In these two features, the amber extract used is advantageously an extract of Baltic amber.

In one particularly advantageous variant, the amber extract is obtained by extraction with an alcoholic or aqueous-alcoholic extraction solvent comprising at least one $C_1$ to $C_5$ monoalcohol and/or at least one $C_2$ to $C_5$ glycol.

Such an extraction solvent is advantageously selected from the group consisting of ethanol, butylene glycol and ethanol/water, butylene glycol/water and butylene glycol/ethanol/water mixtures, preferably an ethanol/water mixture comprising from 40 to 80% of ethanol, butylene glycol, a 50/50 butylene glycol/water mixture or an 80/20 to 60/40 butylene glycol/ethanol mixture.

The amber extract used within the framework of the present invention will advantageously be obtained with an alcoholic extraction solvent whose dry extract is then mixed with a cosmetically acceptable glycolic solvent, particularly butylene glycol.

Said alcoholic extracts will be obtained as follows: Amber, particularly yellow Baltic amber, is reduced to powder and extracted with a $C_1$ to $C_5$ alcohol or a mixture of water and a $C_1$ to $C_5$ alcohol, particularly ethanol and more particularly a mixture of ethanol and water containing 40 to 80% by volume of ethanol. This action is effected by leaving the amber powder to macerate in the aqueous-alcoholic mixture in the cold for several hours, e.g. about 5 h. The mixture is then heated for several hours, e.g. about 8 hours. The extraction liquid is then collected, e.g. after centrifugation, and advantageously filtered to remove the solid residues. The solvent is then driven off, preferably by evaporation under vacuum, to give a so-called alcoholic extract in powder form. This very fine powder is then solubilized or dispersed in a cosmetically acceptable solvent, particularly a glycol and preferably butylene glycol, or a mixture of surfactants.

In another variant, a so-called glycolic extract is prepared. Such an extract is also prepared from amber, preferably yellow Baltic amber, which is reduced to powder and then left to macerate in a glycolic solvent in the cold for about 48 h, preferably with agitation. A hot extraction is then carried out, preferably for about 6 h. A solid-liquid separation is then effected, preferably by centrifugation, after which the supernatant liquid is recovered and filtered to remove the fine particles that may be suspended in this liquid. A preferred extract according to the invention is obtained in this way.

The glycolic solvents used are preferably butylene glycol, a 50/50 by volume butylene glycol/water mixture or an 80/20 to 60/40 by volume butylene glycol/alcohol mixture.

As explained previously, amber extracts are chosen for the preparation of the compositions of the invention as a result of their particular value in improving skin firmness, said value having been confirmed by biological tests which showed the effect of these extracts on the gene expression of human dermal fibroblasts; this is apparent from the Examples, which clearly show the effect of this extract on:

collagenase or type 1 metalloproteinase, called MMP1, the proportion of major collagens in the dermis, particularly collagens 1, 3 and 5 and more particularly collagen 5, which acts on the orientation of the dermal fibers, dermatopontin, which is known for governing the protein/extracellular matrix relationships in the dermis, and small leucine rich proteoglycans (SLRP), particularly biglycan and versican, these being proteoglycans involved in fibrillogenesis, which plays a fundamental role in maintaining the biomechanical properties of the skin.

Apart from the amber extract as defined above, the compositions of the invention contain at least one other active agent selected from the group comprising extracts of *Bertholletia excelsa*, extracts of *Potentilla erecta*, magnesium aspartate, peptides acting on muscle contraction, particularly acetyl hexapeptide 3, peptides and their derivatives grafted with a fatty acid, particularly a $C_{16}$ fatty acid, promoting collagen synthesis, particularly palmitoyl oligopeptide pentapeptide 3 or palmitoyl tetrapeptide 7, soy flour hydrolyzates and plant glyco-lipids, particularly cereal glycosphingolipids and more particularly wheat glycosphingolipids.

The particular action imparted and the preferred proportions of each of these other "active agents" in the composition of the invention are given below:

1) extract of *Bertholletia excelsa*: This is preferably an extract of the pericarp of the fruit. The mode of action and the value of such an extract are described in international patent application WO 96/25143 and French patent application FR 2 752 527. It is apparent from these two patent applications that such an extract makes it possible to promote collagen synthesis and has an anti-free radical activity, enabling it to be used to combat the effects of skin ageing and to prevent the appearance of wrinkles or reduce their depth, or to promote skin firming. Such an extract is advantageously used in the compositions of the invention at a concentration of between 0.1 and 2% by weight.

2) extract of *Potentilla erecta*: Such an extract is described in particular in European patent EP 0 946 138, from which it is apparent that this extract can advantageously be used to promote the cohesion between the dermis and the epidermis by strengthening the dermo-epidermal junction, but also that it makes it possible to stimulate collagen VII formation, these two actions combining to firm the skin, prevent or delay the appearance of the signs of skin ageing, delay the appearance of wrinkles or reduce their depth. A glycolic extract of *Potentilla erecta* will preferably be used in the compositions of the present invention at a concentration of between 0.1 and 2% by weight.

3) magnesium aspartate, at a concentration preferably of between 0.01 and 0.5% and particularly preferably of between 0.02 and 0.1% by weight, based on the composition.

4) peptides for slowing down the release of neuromediators and capable of promoting muscle contraction, particularly acetyl hexapeptide 3, which is better known under the trade name ARGIRELINE® manufactured by Lipotech SA, preferably at a concentration of between 0.1 and 1% by weight, based on the weight of the composition.

5) peptides or peptide derivatives grafted with a fatty acid (particularly $C_{16}$), or a combination of such peptides, for promoting collagen synthesis. Palmitoyl oligopeptide pentapeptide 3 or palmitoyl tetrapeptide 7 will be chosen in particular, at a concentration preferably of between 0.1 and 5% and particularly preferably of between 1 and 3% by weight, based on the total weight of the composition.

6) soy flour hydrolyzates rich in glycoproteins. Such hydrolyzates are commercially available. RAFFERMINE®, marketed by Silab and described as increasing the synthesis of collagen I, fibrillin 1 and fibronectin, may be mentioned in particular. Such a hydrolyzate will be used at a concentration preferably of between 0.1 and 5% by weight and particularly preferably of between 1 and 3.5% by weight, based on the weight of the cosmetic composition.

7) plant glycolipids, particularly cereal glycosphingolipids and especially wheat glycosphingolipids. These glycolipids, and very particularly wheat glyco-sphingolipids, constitute the preferred constituents used as the second active agent in the composition. They impart optimal effects to the composition by acting on the epidermal cells.

They will be used at concentrations preferably of between 0.01 and 5% by weight and particularly preferably of between 0.05 and 0.8% by weight.

The cosmetic compositions of the invention will advantageously contain about 2% by weight of glycolic extracts of amber and about 0.1% by weight of glycosphingolipids, particularly glycosphingolipids extracted from wheat.

The extracts containing glycosphingolipids used will preferably be extracts containing glycosylceramides, digalactosyldiglyceride, triglycerides and phospholipids. These extracts will advantageously contain about 50% by weight of glycosylceramides, 40% of digalactosyldiglycerides, 0 to 5% of triglycerides and 5 to 10% of phospholipids.

It will be advantageous to use mixtures of glycosphingolipids having a fatty acid distribution of around 50 to 65% of linoleic acid, 15 to 20% of palmitic acid and 10 to 15% of oleic acid.

The compositions of the invention can also contain other active agents, particularly:

protectors of the mitochondrion, particularly the mitochondrial DNA, such as hexapeptide 11, at a concentration generally of between 0.1 and 5% by weight and preferably of between 0.5 and 2% by weight, or tocopherol gentisate, at a concentration generally of between 0.01 and 2% by weight.

tocotrienol and derivatives thereof, at a concentration generally of between 0.01 and 5% by weight and preferably of between 0.02 and 0.5% by weight.

an extract of *Rumex crispus*, at a concentration generally of between 0.1 and 5% by weight and preferably of between 0.5 and 2%.

an extract of the rhizome of *Glycyrrhiza glabra*, at a concentration generally of between 0.01 and 1% by weight.

glycosylated or non-glycosylated triterpene derivatives extracted from *Centella asiatica*, particularly madecassoside, asiaticoside, asiatic acid or madecassic acid, by themselves or in combination, at concentrations generally of between 0.1 and 5% by weight.

tocopherol and derivatives thereof, particularly tocopherol phosphate or acetate, at between 0.1 and 0.5% by weight.

ascorbic acid, or vitamin C, known in particular for promoting elastin synthesis. Its action on elastin synthesis is described in French patent FR 2 737 971. Ascorbic acid is introduced into the compositions of the invention at a concentration preferably of between 0.1 and 5% by weight and particularly preferably of between 1 and 2% by weight.

hyaluronic acid or sodium salts thereof, preferably at a concentration of between 0.1 and 5% by weight.

D-xylose, whose use is described in European patent EP 1 028 705, is advantageously contained in the compositions of the present invention at a concentration of between 0.1 and 1% by weight.

glycols, particularly butylene glycol and glycerol, at concentrations of between 1 and 5% by weight.

retinoic acid, at a concentration of between 0.01 and 1% by weight, or retinol or esters thereof, such as retinol propionate, at a concentration generally of between 1500 and 2500 IU.

DNA hydrolyzates, particularly those resulting from the transformation of fish semen extracts, at between 0.01 and 1% by weight.

ecdysteroids of vegetable origin, at concentrations of between 0.1 and 2% by weight.

an oxazolidone, particularly 4-decyloxazolidin-2-one, advantageously at a concentration of between 0.1 and 5% by weight.

plant proteins or plant protein hydrolyzates having a tightening action on the surface of the skin, particularly wheat proteins and/or oat proteins. These proteins are advantageously used in compositions of the invention at concentrations of between 0.1 and 5% by weight.

In all these compositions, the amber extract is advantageously at a concentration of between 0.01 and 5% by weight. Preferably, the concentration of amber extract is between 0.01 and 0.1% by weight if it is an alcoholic extract, and between 0.5 and 5% by weight, preferably between 1 and 2.5% by weight, if it is a glycolic extract as defined above.

The following will preferably be selected from the complementary active agents mentioned above: an extract of *Rumex crispus*, an extract of the rhizome of *Glycyrrhiza glabra*, a glycosylated or non-glycosylated triterpene derivative, an extract of *Centella asiatica*, particularly madecassoside, asiaticoside, asiatic acid or madecassic acid, by itself or in combination, a DNA hydrolyzate, particularly that obtained from a fish semen extract, and an oxazolidone, particularly 4-decyloxazolidin-2-one, these various agents preferably being employed in the proportions indicated above and preferably in compositions which contain a wheat sphingolipid extract as the second cosmetic active agent.

In one advantageous variant, the amber extract is incorporated in a vector system that allows a programmed release of the active agent, particularly in a lamellar vesicle of the liposome type.

The advantages of the composition of the invention will become more clearly apparent from the Examples given below.

EXAMPLE 1

Preparation of an Ethanolic Amber Extract

Yellow Baltic amber is reduced to powder and extracted with a 60% by volume ethanol/water mixture (ratio 1:10 v/v, based on the amber) by maceration in the cold for 5 hours, followed by heating for 8 hours. The mixture is centrifuged and the extraction liquid is recovered and filtered to remove the smallest particles. The resulting extract can be used.

EXAMPLE 2

Following the procedure of Example 1, the alcoholic extract is reduced to dryness by evaporation under vacuum to give a very fine powder that is soluble or dispersible in cosmetically acceptable solvents, such as glycols, or surfactant systems. In this case 0.5% by weight of dry extract is mixed with butylene glycol and the whole can be formulated at 2% by weight of the final composition.

EXAMPLE 3

Preparation of a Glycolic Extract of Baltic Amber

Yellow Baltic amber is reduced to powder, left to macerate in butylene glycol in the cold for 48 hours, with agitation, and then extracted under the action of heat for 6 hours. A solid-liquid separation is effected by centrifugation, the extraction liquid is recovered by pumping the supernatant and filtered to remove the smallest particles, and the glycolic extract forming the subject of the invention is recovered.

EXAMPLE 4

Demonstration of the Action of an Amber Extract on the Gene Expression of Human Dermal Fibroblasts Cultivated in a Monolayer 1) Materials and Methods a) Cell Culture Normal human fibroblasts (NHF) are thawed and then inoculated on a 75 cm$^2$ plate at a rate of 10$^6$ cells per plate in DMEM (Dulbecco's modified Eagle's medium) containing 10% (v/v) of fetal calf serum (FCS). When confluence is reached, the cells are treated with a trypsin solution and 8 plates are then inoculated. When confluence is reached, the NHF are rinsed 3 times with a phosphate buffer (phosphate buffered saline, PBS) and then incubated for 18 h in DMEM without FCS.

b) Treatment with Amber

After 18 h of serum-free culture, the cells are treated according to different conditions:
2% amber extract according to Example 1 (v/v)
solvent (butylene glycol), 2% (v/v)
DMEM alone (positive control)
After 4 hours of culture, the total RNAs are extracted.

c) Extraction of the Total RNAs

After incubation, the culture media are discarded and the cells are then placed on a bed of ice, without prior rinsing.

Under a chemical hood, the cells are scraped off and lyzed in 1 ml of RNAplus (sold by Qbiogene Inc) and the whole is recovered in a 1.5 ml Eppendorff tube.

The total RNAs are then assayed with an Agilent 2100 analyzer.

d) Amplification of the RNAs and Labeling

An RNA amplification step is required prior to the hybridization step and is carried out according to a protocol already described by Eberwine (Eberwine, J. (1996). Amplification of mRNA populations using aRNA generated from immobilized oligo(dT)-T7 primed cDNA. *Biotechniques*, 20, 584-591). The different samples of amplified RNAs (hereafter designated by aRNAs) are then quantified by spectrophotometry (Bioanalyzer 2001, Agilent).

1 μg of aRNAs from the untreated samples and the samples treated with amber extract are labeled by reverse transcription with the fluorophores Cy5 and Cy3 respectively. These labeled samples of complementary DNA (hereafter designated by acDNA) are then hybridized on a biochip specific for the genes expressed in the skin in order to disclose the genes modulated by the amber extract. A PIQOR™ Microarrays biochip (reference 160-000-681) was used here.

e) Hybridization and Data Analysis

A hybridization is carried out for 16 hours on a hybridization station, after which the data are analyzed as described in detail by Bosio et al. (Bosio, A., Knorr, C., Janssen, U., Gebel, S., Haussmann, H. J. and Muller, T. (2002). Kinetics of gene expression profiling in Swiss 3T3 cells exposed to aqueous extracts of cigarette smoke. *Carcinogenesis* 23, 741-748). Briefly, the image capture and the quantification of the fluorescence signals are performed with a ScanArrayLite apparatus (Packard Bioscience, Billerica, Mass., USA) and Ima-Gene 4.1 software (BioDiscovery, Los Angeles, Calif., USA). The local background noise was subtracted from the signal to give its nett intensity, enabling the ratio Cy5/Cy3 to be determined. The means of the fluorescences of the 4 spots corresponding to the same acDNA are subsequently calculated and then normalized by linear regression (LOWESS normalization method). Thereafter, only the genes showing a nett intensity that is twice the magnitude of the background noise are retained for analysis.

2) Results

The results obtained after analysis of the different biochips show that the amber extract has a significant effect on modulation of the expression of certain genes expressed by the NHF in the skin.

In fact, analysis of the biochips discloses a significant variation in response to the amber extract:
on the expression of collagenase-1 or MMP-1: an inhibitory effect on the expression of collagenase by the NHF is actually observed, relative to the control, the amount expressed being 60% (compared with 100% for the control),
on the synthesis of collagens of types I, III and V: more precisely, the following activations are observed, relative to the control (100%):
collagen I—alpha 1 chain: 175%,
collagen I—alpha 2 chain: 250%,
collagen III: 221%, relative to the control,
collagen V—alpha 1 chain: 200% activation, relative to the control,
collagen V—alpha 2 chain: 220% activation, relative to the control,
on the expression of dermopontin: an activating effect in the order of 210% is observed, relative to the control,
on the expression of biglycan and versican: respective activations of 200% and 300% are observed, relative to the control.

EXAMPLE 5

Compositions According to the Invention

In the compositions exemplified below, the indicated contents of amber extract are in percentages by weight.

a) Firming Gel:

Amber extract (butylene glycol according to Example 3): 4

Wheat glycosphingolipids: 0.2

(wheat cerasomes sold by E.P.I. France)

Glycerol: 2

Preservatives and perfumes: 0.3

Excipient qsp 100 b) Firming Lotion:

Amber extract (ethanol according to Example 1): 0.1

Wheat glycosphingolipids: 0.15

(wheat cerasomes sold by E.P.I. France)

Preservatives and perfumes: 0.3

Excipient qsp 100 c) Firming Cream:

Amber extract (butylene glycol according to Example 3): 2

Extract of *Bertholletia:* 1

Glycolic extract of *Potentilla erecta:* 0.5

Palmitoyl oligopeptide pentapeptide 3: 3

Wheat glycosphingolipids: 0.2

(wheat cerasomes sold by E.P.I. France)

Tocopherol acetate: 0.2

Glycerol: 2

4-Decyloxazolidin-2-one: 1

Preservatives and perfumes: 0.3

Excipient qsp 100

This emulsion is used once or twice a day on the face, where it gradually retightens the lines.

d) Tightening Serum for the Lower Face and Neck:

Amber extract (butylene glycol according to Example 3): 3

Extract of *Bertholletia:* 1

Glycolic extract of *Potentilla erecta:* 0.5

Oat proteins: 2

Palmitoyl oligopeptide pentapeptide 3: 3

Glycosphingolipids: 0.2

Extract of *Glycyrrhiza glabra:* 0.1

Tocopherol acetate: 0.2

Micronized titanium oxide: 0.5

4-Decyloxazolidin-2-one: 1

Preservatives and perfumes: 0.3

Excipient qsp 100

This tightening serum, to be applied in the morning, associates an immediate effect with a basic care effect.

e) Film Patch:

Amber extract (butylene glycol according to Example 3): 1.5

Extract of *Bertholletia:* 1

Magnesium aspartate: 0.1

Glycolic extract of *Potentilla erecta:* 0.5

Palmitoyl oligopeptide pentapeptide 3: 3

Glycosphingolipids: 0.2

Extract of *Glycyrrhiza glabra:* 0.1

Polymers: 2

Tocopherol acetate: 0.2

Glycerol: 1

4-Decyloxazolidin-2-one: 0.8

Preservatives: 0.2

Perfumed excipient qsp 100

This film patch is applied to the lower face and neck in the evening on retiring.

f) Care Ampoules:

Amber extract (butylene glycol according to Example 3): 5

Extract of *Bertholletia:* 1

Glycolic extract of *Potentilla erecta:* 0.5

Glycosphingolipids: 0.2

Stabilized ascorbic acid: 0.5

Hyaluronic acid solution: 2

Protein hydrolyzate: 1

Solubilizing system: 1.5

This care in ampoule form is applied in a 21-day course of treatment for a deep action to retighten the tissues.

What is claimed is:

1. A cosmetic composition comprising the following as active agents:
a first active agent consisting of an amber extract, and
a second active agent consisting of cereal glycosphingolipids,
wherein said amber extract is obtained by the extraction of amber, with an alcoholic or aqueous-alcoholic extraction solvent comprising at least one C1 to C5 monoalcohol and/or at least one C2 to C5 glycol, and
said composition comprises from 0.01 to 5% by weight of said amber extract and from 0.05 to 0.8% by weight of cereal glycosphingolipids.

2. The composition according to claim 1 wherein said extraction solvent is selected from the group consisting of ethanol, butylene glycol and ethanol/water, butylene glycol/water and butylene glycol/ethanol/water mixtures.

3. The composition according to claim 1 which also comprises at least one active agent selected from the group consisting of an extract of *Rumex crispus*, an extract of the rhizome of *Glycyrrhiza glabra*, a glycosylated or non-glycosylated triterpene derivative, an extract of *Centella asiatica*, a DNA hydrolyzate, and an oxazolidone.

4. A composition according to claim 1 wherein the amber extract is incorporated in a vector system that allows a programmed release of the active agent.

5. A method of cosmetic care, comprising applying to the skin of a subject in need thereof a cosmetic composition as claimed in claim 1.

6. The composition according to claim 1, wherein the cereal glycosphingolipids are wheat glycosphingolipids.

7. The composition according to claim 1, wherein said composition comprises 2% by weight of said amber extract and 0.1% by weight of cereal glycosphingolipids.

8. The composition according to claim 1, wherein said cereal glycosphingolipids comprise glycosylceramides, digalactosyldiglycerides, triglycerides and phospholipids.

9. The composition according to claim 1, wherein said cereal glycosphingolipids comprise a fatty acid distribution of around 50 to 65% of linoleic acid, 15 to 20% of palmitic acid, and 10 to 15% of oleic acid.

* * * * *